United States Patent
Wilson

(10) Patent No.: US 6,735,467 B2
(45) Date of Patent: May 11, 2004

(54) METHOD AND SYSTEM FOR DETECTING SEIZURES USING ELECTROENCEPHALOGRAMS

(75) Inventor: Scott B. Wilson, Del Mar, CA (US)

(73) Assignee: Persyst Development Corporation, Prescott, AZ (US)

( * ) Notice: Subject to any disclaimer, the term of this patent is extended or adjusted under 35 U.S.C. 154(b) by 197 days.

(21) Appl. No.: 10/123,834

(22) Filed: Apr. 15, 2002

(65) Prior Publication Data

US 2003/0195429 A1 Oct. 16, 2003

(51) Int. Cl.$^7$ ............................................. A61B 5/0476
(52) U.S. Cl. ...................................... 600/544; 128/925
(58) Field of Search .......................... 600/544; 128/920, 128/925; 702/19

(56) References Cited

U.S. PATENT DOCUMENTS

| | | | | |
|---|---|---|---|---|
| 5,311,876 A | * | 5/1994 | Olsen et al. ................. | 600/544 |
| 6,337,997 B1 | | 1/2002 | Rise | |
| 6,442,421 B1 | * | 8/2002 | Le Van Quyen et al. ... | 600/544 |
| 6,594,524 B2 | * | 7/2003 | Esteller et al. .............. | 600/544 |
| 6,658,287 B1 | * | 12/2003 | Litt et al. .................... | 600/544 |

OTHER PUBLICATIONS

Blanco, S, et al., "Applying Time–Frequency Analysis to Seizure EEG Activity," *IEEE Eng. Med. Biol. Mag.* 16(1):64–71 (1997).

Bodenstein, G., et al., "Computerized EEG Pattern Classification by Adaptive Segmentation and Probability–Density–Function Classification. Description of the Method" *Comput. Biol. Med.* 15(5):297–312 (1985).

Bullmore, E. et al., "A New Technique for Fractal Analysis Applied to Human, Intracerebrally Recorded, Ictal Electroencephalographic Signals," *Neurosci Lett.* 146(2):227–230 (1992).

Franaszczuk, P.J., "Time–Frequency Analysis Using the Matching Pursuit Algorithm Applied to Seizures Originating From the Mesial Temporal Lobe," *Electroencephalogr Clin. Neurophysiol.* 106(6):513–521 (1998).

Gabor, A.J., "Seizure Detection Using a Self–Organizing Neural Network: Validation and Comparison with Other Detection Strategies," *Electroencephalogr Clin Neurophysiol*, 107(1):27–32 (1998).

Gabor, A.J., et al., "Automated Seizure Detection Using a Self–Organizing Neural Network," *Electroencephalogr Clin. Neurophysiol.* 99(3):257–266 (1996).

Geva, A.B., et al., "Forecasting Generalized Epileptic Seizures From the EEG Signal by Wavelet Analysis and Dynamic Unsupervised Fuzzy Clustering," *IEEE Trans. Biomed. Eng.* 40(10):1205–1216 (1998).

Geva, A.B., "Feature Extraction and State Identification in Biomedical Signals Using Hierarchical Fuzzy Clustering," *Med. Biol. Eng. Comput.* 36(5):608–614 (1998).

Gotman, J., et al., "Automatic Recognition and Qualification of Interictal Epileptic Activity in the Human Scalp EEG," *Electoencephalogr Clin. Neurophysiol.* 41(5):513–529 (1976).

Gotman, J., et al., "Automatic Recognition of Epileptic Seizures in the EEG," *Electoencephalogr Clin. Neurophysiol.* 54:530–540 (1982).

(List continued on next page.)

Primary Examiner—Eric F. Winakur
(74) Attorney, Agent, or Firm—Noel C. Gillespie, Esq.; Amy E. Simpson, Esq.

(57) ABSTRACT

A method and a system are provided for detection of seizures by applying advanced numerical analysis techniques to digitized waveforms of an electroencephalogram (EEG) recording. In an embodiment, the advanced numerical analysis techniques implemented in the method and system for detecting seizures include a combination of matching pursuit, neural network rules, and connected-object clustering algorithms.

45 Claims, 5 Drawing Sheets

OTHER PUBLICATIONS

Hilfiker, P., et al., "Detection and Evolution of Rhythmic Components in Ictal EEG Using Short Segment Spectra and Discriminant Analysis," *Electoencephalogr Clin. Neurophysiol* 82(4):255–265 (1992).

Hofmann, W.G., et al., "Unsupervised Classification of EEG From Subdural Seizure Recordings," *Brain Topogr.* 10(2):121–132 (1997).

Jing, H., et al., "Comparison of Human Ictal, Interictal and Normal Non–linear Component Analyses," *Clin. Neurophysiol* 111(7):1282–1292 (2000).

Klatchko, A., et al., "Enhancing the Detection of Seizures with a Clustering Algorithm," *Electoencephalogr Clin. Neurophysiol.* 106(1):52–63 (1998).

Liu, A., et al., "Detection of Neonatal Seizures Through Computerized EEG Analysis," *Electoencephalogr Clin. Neurophysiol* 82(1):30–37 (1992).

Osorio, I, et al., "Real–Time Automated Detection and Quantitative Analysis of Seizures and Short–Term Prediction of Clinical Onset," *Epilepsia* 39(6):615–627 (1998).

Park, H.S., "Detection of Epileptiform Activities in the EEG Using Neural Network and Expert System," *Medinfo.* 9(2): 1255–1259 (1998).

Penczek, P., et al., "Computer–aided Analysis of the Epileptic EEG," *Acta. Physiol. Pol.* 37(6):262–274 (1986).

Qu, H., et al., "A Patient–Specific Algorithm for the Detection of Seizure Onset in Long–Term EEG Monitoring: Possible Use as a Warning Device," *IEEE Trans Biomed. Eng.* 44(2): 115–122 (1997).

Wilson, S.B., et al., "Spike Detection IV: Reduction of Model Complexity Via Small Neural Networks Constrained by Domain Expertise," Abstract:1–18 (2002).

Wu, L., et al., "Segmentation and Classification of EEG During Epileptic Seizures," *Electroencephalogr Clin. Neurophysiol* 106(4):344–356 (1998).

Akay, M., "Detection and Estimation Methods for Biomedical Signals," *San Diego: Academic Press* xiv(268) 186–191 (1996).

Akay, M., "Time Frequency and Wavelets in Biomedical Signal Processing," *IEEE Press* xxviii(739) 398–399(1998).

Jain, A.K., et al., "Algortihms for Clustering Data," xiv(320)54–59 (1998).

Komzak, J., "Hierarchical Clustering Speed Up Using Position Lists and Data Position Hierarchy," http://www.kmi.open.ac.uk/papers/kmi–tr–115.pdf, (2001).

Mallat, S.G., "A Wavelet Tour of Signal Processing," xxiv(637)420–423 (1999).

Wickerhauser, M.V. "Adapted Wavelet Analysis from Theory to Software," xii(486)272–275,416–418 (1994).

* cited by examiner

US 6,735,467 B2

METHOD AND SYSTEM FOR DETECTING SEIZURES USING ELECTROENCEPHALOGRAMS

BACKGROUND OF THE INVENTION

1. Field of the Invention

The present invention relates to detection of seizures, and more particularly, to detection of seizures with advanced algorithms.

2. Background Art

Epilepsy is a condition characterized by recurrent seizures which are the outward manifestation of excessive or hyper-synchronous abnormal electrical activity of neurons in the cerebral cortex of the brain. A seizure patient may suffer from several different types of seizures, or any combination thereof. For example, a common type of epilepsy is called the grand mal seizure, which is manifested by symptoms of convulsions with tonic-clonic contractions of muscles. Another type of epilepsy is called the absence seizure, which is characterized by brief and sudden loss of consciousness. Other types of seizures include complex partial seizure, which is characterized by a complete loss of consciousness, and psychomotor seizure, which is characterized by clouding of consciousness for one to two minutes. Some types of seizures may involve the entire brain, while other types of seizures may affect only a local portion of the brain.

Electroencephalograms (EEGs) have been employed to record electrical signals generated by different parts of the brain. In a typical EEG, a plurality of electrodes are placed across the scalp of a seizure patient with predetermined spacings. FIG. 1 shows a diagram illustrating a typical arrangement of electrodes positioned on the scalp of an epilepsy patient along standard lines of measurements. Voltages measured across predetermined pairs of electrodes, for example, C3-F3, F3-F7, F7-T3, T3-T5, etc., are measured simultaneously and recorded as waveforms over a long period of time. Such simultaneous recording of voltage waveforms across different pairs of electrodes is commonly referred to as a montage, a typical example of which is illustrated in FIG. 2. The voltage waveform across a given pair of electrodes in the montage of an EEG recording is commonly referred to as a channel. A seizure is typically manifested by a highly rhythmic pattern of voltage waveforms on an EEG recording. However, depending upon the individual patient, different types of seizures, and various other factors, an onset of seizure is sometimes not readily discernable by a human reader from a montage of an EEG recording. For example, sometimes a seizure may manifest itself as a random waveform pattern across a montage of an EEG recording. Sometimes recording errors may occur in one or more channels of a montage of an EEG recording. Sometimes an onset of seizure is not shown on an EEG recording as a rhythmic pattern of waveforms, but rather as an abnormal change from the background waveform pattern.

A human reader of an EEG recording may need to go through hours or even days of recorded waveforms to determine the onset, duration, and type of seizures that may have occurred during that time. The human reader may miss an occurrence of a seizure, which is referred to as a false negative, or may mark a segment of the waveforms as a seizure event, which is referred to as a false positive.

Conventional algorithms have been developed to assist a human reader in detecting seizures using traditional fast Fourier transform (FFT) or other spectral analysis techniques. While these traditional techniques are usually effective in detecting highly rhythmic patterns of waveforms in order to identify a seizure event, some types of seizures which are not manifested by such highly rhythmic patterns may still be missed. Signal processing using conventional spectral analysis techniques may also sometimes return false positives, depending upon the perimeters set by the algorithm.

Therefore, there is a need for an improved system and method for detecting seizures from EEG recordings with a high degree of reliability.

SUMMARY OF THE INVENTION

The present invention provides a method of detecting a seizure, generally comprising the steps of:

(a) dividing a digitized waveform of an electroencephalogram (EEG) recording into a plurality of epochs each having a first predetermined duration;

(b) computing matching pursuit for a given one of the epochs to obtain a plurality of seizure atoms;

(c) describing the seizure atoms and the given epoch with at least one neural network (NN) rule;

(d) applying connected-object clustering to the epochs in a sliding window of a second predetermined duration to obtain a clustering result; and (e) establishing a seizure point from the clustering result.

Advantageously, the method in an embodiment according to the present invention which utilizes advanced numerical analysis techniques including matching pursuit, neural network rules and connected-object clustering is capable of improving seizure detection with a high degree of accuracy and reliability.

BRIEF DESCRIPTION OF THE DRAWINGS

The present invention will be described with particular embodiments thereof, and references will be made to the drawings in which.

DETAILED DESCRIPTION

Figure 1:
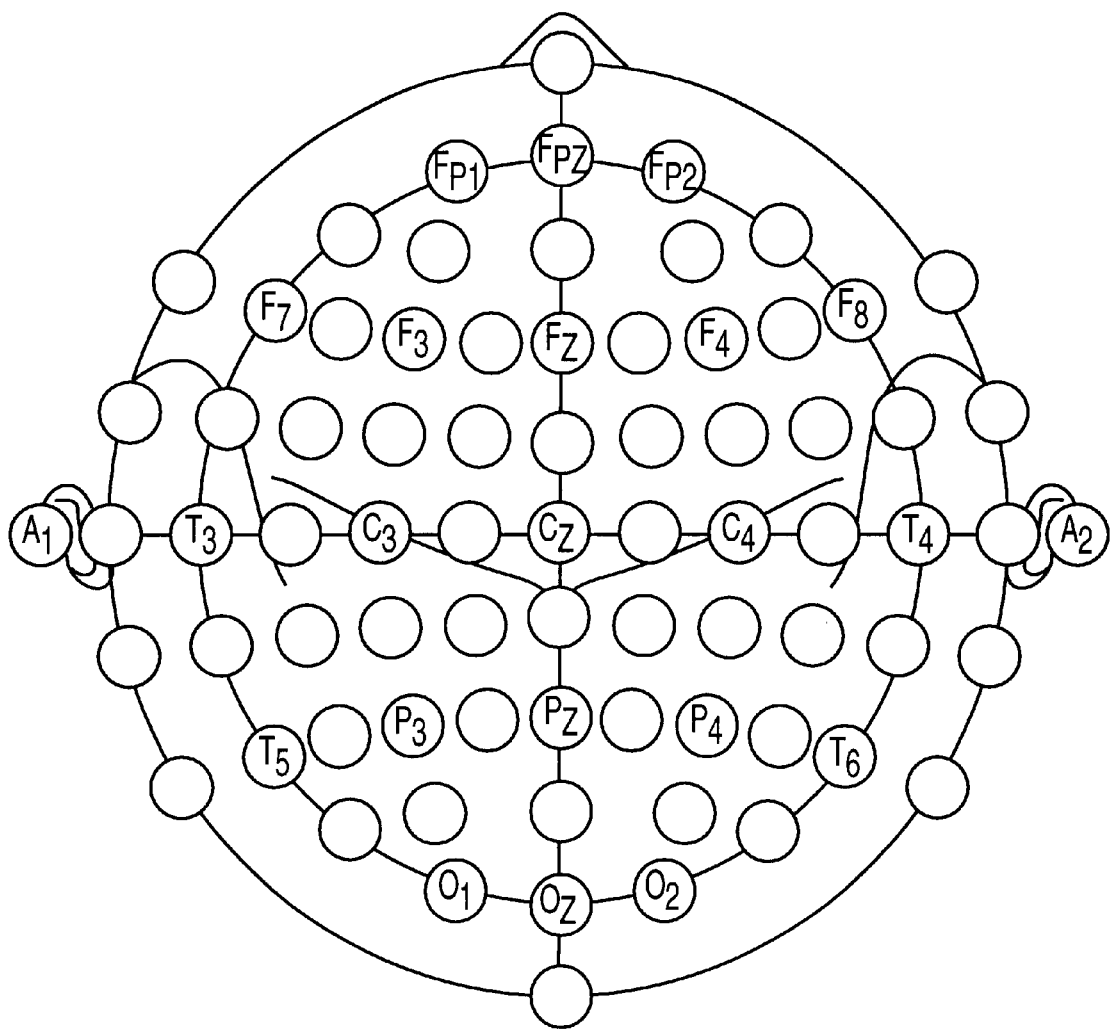
FIG. 1 is a diagram illustrating a typical arrangement of electrodes positioned on the scalp of an epilepsy patient.
Figure 3:
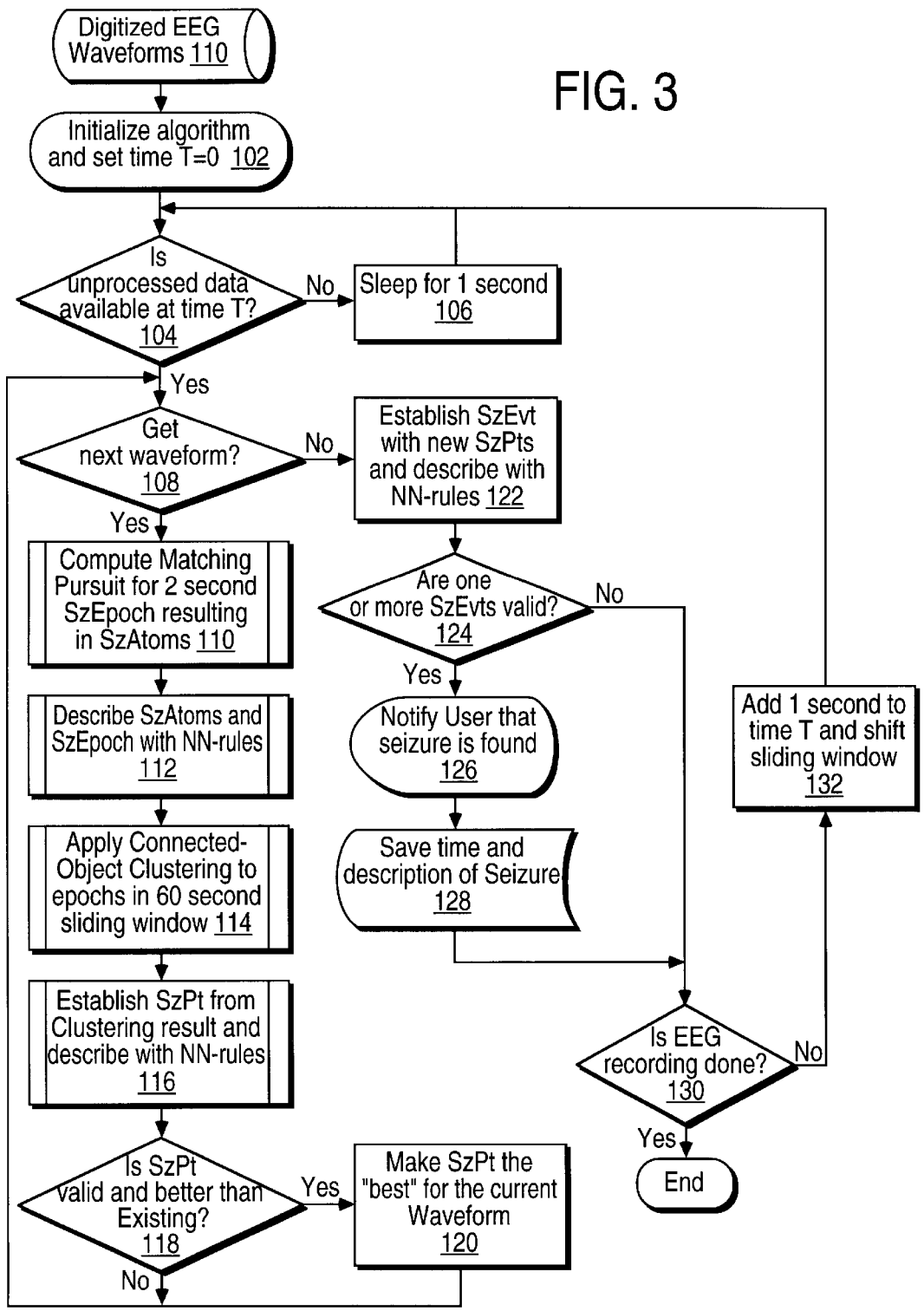
FIG. 3 is a flow chart illustrating an embodiment of a method for detecting seizures according to the present invention.

FIG. 3 is a flow chart illustrating a method of seizure detection using advanced numerical algorithms in an embodiment according to the present invention. Initially, digitized waveforms of an electroencephalogram (EEG) recording indicated by block 100 is received by a computer which processes these waveforms to detect seizure events. In this patent application, a singular waveform is defined as one of a plurality of waveforms of an EEG recording measured across a given pair of electrodes as illustrated in FIG. 1. An EEG recording typically includes a plurality of voltage waveforms recorded simultaneously across a plurality of predetermined pairs of electrodes. A simultaneous recording of such multiple waveforms across multiple pairs of electrodes is commonly referred to as a montage. The waveform measured across each designated pair of electrodes for indicating activity in a given region of the brain is commonly referred to as a channel.

Figure 2:
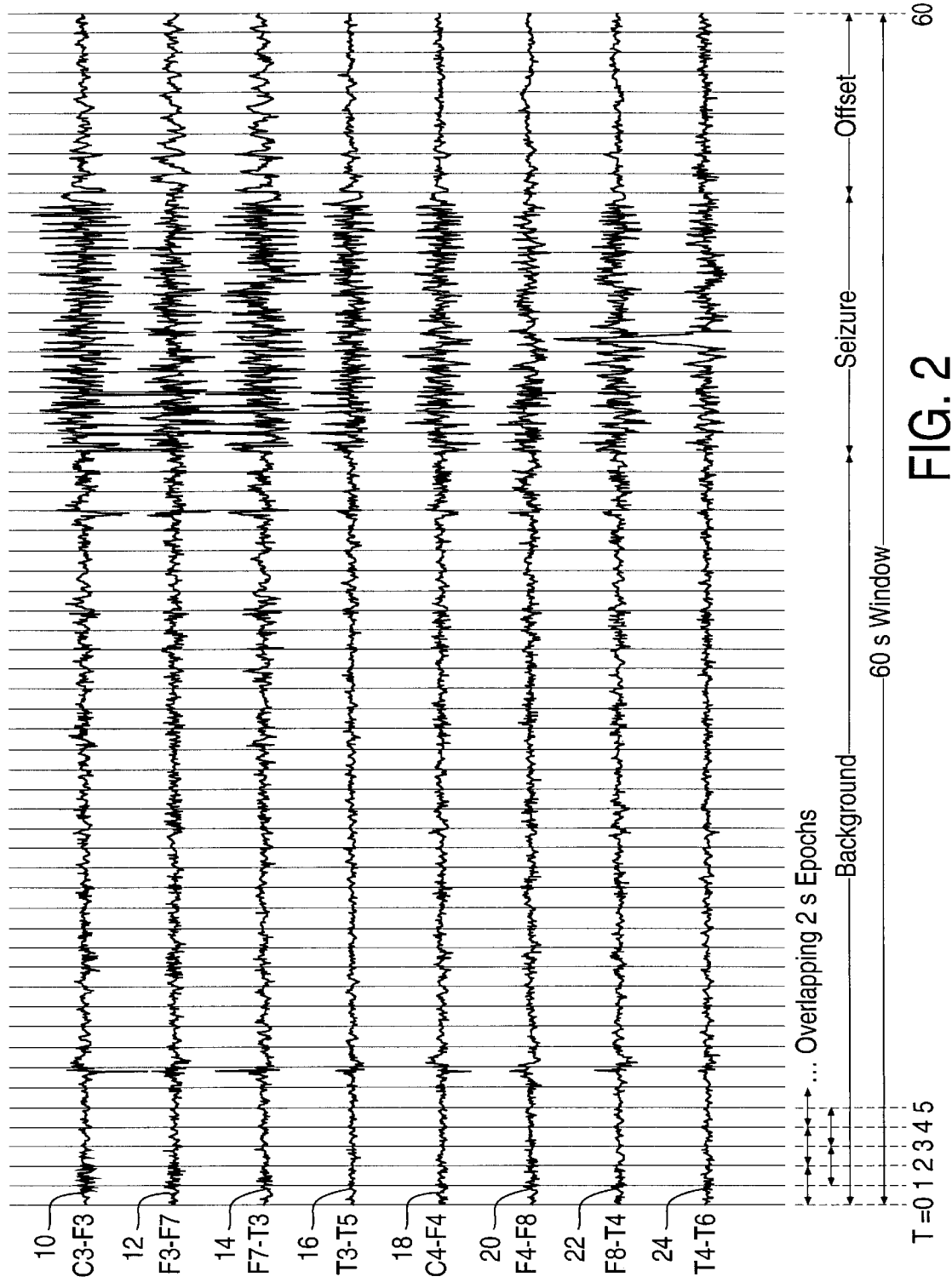
FIG. 2 shows a typical montage of an EEG recording with eight channels of voltage waveforms across eight pairs of electrodes.

FIG. 2 illustrates a typical montage of an EEG recording with eight channels of simultaneous waveforms recorded over a given period of time. For example, a first waveform 10 in FIG. 2 is a voltage waveform measured across a pair of electrodes C3 and F3 in FIG. 1, while a second waveform 12 in FIG. 2 is a voltage waveform measured across another pair of electrodes F3 and F7 in FIG. 1. The remaining waveforms 14, 16, 18, 20, 22, and 24 in FIG. 2 are the voltage waveforms measured across pairs of electrodes F7-T3, T3-T5, C4-F4, F4-F8, F8-T4, and T4-T6, respectively. In FIG. 2, it is assumed that the EEG recording starts at an initial time T=0. The spacing between immediately adjacent vertical lines in the EEG recording of FIG. 2 depicts an interval of one second.

Referring to FIG. 3, after the digitized waveforms of the EEG recording is received by the computer, the algorithm is initialized and the start of the EEG recording is set at a time T=0 as indicated by block 102. The computer then determines whether unprocessed EEG data is available at the time T as indicated by block 104 and causes a time delay or a sleep of a predetermined duration, for example, one second, if unprocessed EEG data is unavailable at the time T, as indicated by block 106.

If unprocessed EEG data is available at the time T, each digitized waveform of the EEG recording is entered for processing in an iterative manner until the processing of all waveforms of the montage of the EEG recording is complete, as indicated by block 108. For example, referring to FIG. 2, the processing of the first waveform 10 is followed by the processing of the second waveform 12 and so on, until the last waveform 24 is processed. For each waveform of the digitized EEG recording, the method according to an embodiment of the present invention utilizes three algorithmic techniques, namely, matching pursuit, small neural network (NN) rules and connected-object hierarchical clustering algorithms as indicated by blocks 110, 112 and 114, respectively, for enhanced seizure detection.

Before each digitized EEG waveform is processed with matching pursuit, small neural network rules and connected-object clustering algorithms, an EEG recording which typically contains EEG data over a period of many hours or even days is divided into relatively small segments of time to facilitate data processing. Typical characteristics of seizures allow for partitioning of time to increase computational efficiency while detecting seizures with a high degree of accuracy. A short seizure lasts for about two seconds.

In an embodiment, a digitized EEG waveform is divided into two-second intervals, each interval commonly referred to as an epoch. To enhance the probability of detection of short-duration seizures, the processing of EEG data is applied to each two-second epoch with a time shift of one second. For example, referring to FIG. 2, matching pursuit is computed for a given waveform for a first epoch of two seconds between times T=0 and T=2, followed by a second epoch between times T=1 and T=3, followed by a third epoch between times T=2 and T=4, and so on. Such an overlap of one second for each successive two-second epoch allows for a greater probability of detection of short-duration seizures.

The matching pursuit algorithm that is applied to each two-second epoch as indicated by block 110 in the flow chart of FIG. 3 is described mathematically in Wickerhauser, *Adapted Wavelet Analysis From Theory to Software*, A. K. Peters, Wellesley, Mass., 1994, and Mallat, *A Wavelet Tour of Signal Processing*, Academic Press, San Diego, 1999, both of which are incorporated herein by reference.

The matching pursuit algorithm has been developed as a result of the desire to improve the time and frequency resolution of traditional fast Fourier transform (FFT) algorithms. It is well known in the art that wavelets typically give high-frequency bands better time resolution with corresponding loss in frequency resolution. It is also well known in the art that wavelet packets typically allow the time-frequency resolution to fit to the signal for different frequency bands, thereby resulting in a trade-off between the frequency resolution and the time resolution within a given frequency band. For example, with conventional wavelet packet processing, each frequency band may be processed with a high frequency resolution and a low time resolution, or alternatively, with a low frequency resolution and a high time resolution. The matching pursuit algorithm, which is an improvement over conventional wavelet packet algorithms, affords complete flexibility to different parts of signals, even within the same frequency band, in a trade-off between frequency resolution and time resolution.

The matching pursuit algorithm proceeds by decomposing the original EEG waveform into a sum of orthogonal "atoms" that are localized in time and frequency: $f(t)=\Sigma a_I g_I(t)$. The atoms have the form $$g_I(t) = \frac{1}{\sqrt{s}} g\left(\frac{t-u}{s}\right) e^{-ivt},$$

where t is time, s>0 is the scale, u is the translation and v is the frequency. The index I=(s, v, u) describes the chosen set of parameters. If $g(t)=e^{-\pi t^2}$, then $g_I(t)$ is called a Gabor atom, which is a sinusoid of frequency v with an exponentially localized time window centered on u. From the set of all possible atoms, called the Gabor dictionary (i.e., all values of the index I), the best single atom is found in each step and then subtracted from the waveform. This continues for a fixed number of iterations or until the error of the residual waveform reaches an acceptable size.

The use of Gabor atoms as described above offers precise time-frequency resolution, but it is relatively slow—about ~22 ms per atom for each two-second epoch of 32 channels sampled at 32 Hz on a 866 MHz processor coded in C++. A faster version of matching pursuit is achieved by using a wavelet packet dictionary in place of the Gabor dictionary. (Like the Gabor dictionary, the wavelet packet is a redundant division of the time-frequency plane into various sized rectangles.) This results in a speed improvement of about eighteen times with some loss in resolution, which is usually acceptable in seizure detection applications.

After the matching pursuit algorithm is applied to each two-second epoch (SzEpoch) by decomposing the epochs of the EEG waveform into atoms (SzAtoms), the seizure atoms and the seizure epoch are described with one or more neural network (NN) rules, as indicated by block 112 in the flow chart of FIG. 3. Small neural networks can be combined with domain expertise to create NN rules, which are similar to expert system rules that propagate the strength or uncertainty in the inputs to the NN. A mathematical description of such NN rules is described in Wilson et al., *Spike detection: reduction of model complexity via small neural networks constrained by domain expertise, Clinical Neurophysiology*, submitted Mar. 5, 2002. Using this methodology, the NNs are not over-trained and the number of required training samples can be reduced by reducing the model complexity. Tendency rules are used to encode weak expert knowledge and describe the general shape of the NN's transfer function, i.e., the graph of the NN inputs vs. output. Inputs are displayed on the x and y axes, and the output is displayed on the z axis. If the NN has more than two inputs, then the other inputs are held constant at their average value, and pairs of inputs are examined. For example, the tendency rule SzRhythm/BkRhythm and SzAmp/BkAmp~>Perception encompasses the general notion that seizures should be more rhythmic and probably at higher voltages compared to the background activity. Any NN-rule which has a transfer function that contradicts this knowledge is not accepted.

Rules are traditionally written in the form if X and Y then Z. Boolean logic describes how to combine these types of rules if X, Y and Z are variables taking the possible values of true and false. Expert and fuzzy systems are developed from rules with the understanding that many interesting problems can best be expressed using non-Boolean variables. They extend Boolean logic to allow rules that propagate the uncertainty and/or strength of the premise to the rule's conclusion. If the rule has only a single conclusion, then the general form of these rules is a function that takes one or more inputs and has a single output, which is the essence of a neural network. If the NN is sufficiently simple, it may be possible to describe it linguistically as one or more rules.

The rules that are developed for detection of seizures in one embodiment are very small NNs consisting of two to five inputs and a single output. Expert knowledge is used to choose the inputs and the related output. After the NN is trained, it is only accepted if the response surface, i.e., what the rule says, is consistent with the expert knowledge. The requirement that the NN be consistent with expert knowledge, rather than simply a "black box," is important to this embodiment. It is preferred that small neural networks that can be analyzed via their response surface be implemented to allow for penetration of the conventional "black box" shell. In contrast, the response surface of a poorly defined network which displays discontinuities or contradicts domain knowledge is undesirable in these applications.

It is typical that an EEG recording includes EEG data recorded over a relatively long period of time, from several hours to several days, for example. The EEG data covering the total time period of many hours or days usually need not be analyzed at once. In an embodiment, connected-object clustering algorithm is applied to a plurality of epochs in a sliding window of a pre-determined duration, for example, 60 seconds, as indicated by block 114 in the flow chart of FIG. 3.

As illustrated in FIG. 2, a sixty-second sliding window includes thirty epochs of two seconds each and initially starts with T=0. The initial sixty-second sliding window covers a time period between T=0 and T=60. After the EEG data for this sixty-second window is processed, the sliding window shifts to the right by one second covering a time period between T=1 and T=61. As the sixty-second sliding window shifts progressively in one-second intervals, EEG data that are older than sixty seconds are discarded. By applying the sliding window to the EEG waveform, connected-object clustering can be performed on the epochs to obtain a clustering result with improved computational speed and efficiency.

One of the complicating aspects of seizure detection is the need to perform two tasks at roughly the same time: to identify the event and to determine its approximate end-points. A novel type of clustering is implemented in an embodiment to identify the onset and approximate duration of an event of brain activity, and then to decide whether the event is a seizure event.

Clustering methods fall into two general categories: hierarchical and partitional (Jain, A. K. and Dubes, R. C., *Algorithms for clustering data*, Englewood Cliffs, N.J., Prentice Hall, 1988). Partitional methods require as input the appropriate number of groups, and the groups found are dependent on the order that the objects are submitted. The computational complexity (i.e., the approximate number of operations) for these algorithms is O(N*K*R), where N is the number of objects, K is the number of groups, and R is the number of iterations. Hierarchical methods generate a nested sequence that allows the appropriate number of groups to be identified interactively, using a dendrogram, for example, or via a heuristic method. The high computational complexity [O(N*N*N)] of hierarchical algorithms makes them undesirable for seizure detection applications. For example, an eight-hour record includes N=28,800 one-second epochs. These requirements can be reduced to O(N*log(M)), where M is the maximum number of groups in the nested structure, by taking advantage of the connected nature of the epochs. The following are the steps of an embodiment of the connected-object clustering algorithm:

Step 1. Given an ordered list of N connected objects, break the list into two groups of k and N−k objects for k=1 . . . N−1. If N=1, then stop this branch of the algorithm.

Step 2. Choose index k to maximize the difference between the two groups. Stop if the desired number of groups is found. Stop this branch of the algorithm if the difference between the two groups is too small.

Step 3. Apply the algorithm to the two resulting groups.

Step 2 requires a function that rates the difference between two groups. The Davies-Bouldin index (Jain, A. K. and Dubes, R. C., *Algorithms for clustering data*, Englewood Cliffs, N.J., Prentice Hall, 1988, p. 186) is used, which was developed as a way to determine the "correct" number of clusters. For K clusters, the index is given by $$DBK = (1/K)\sum_{k=1}^{K} \max_{j \neq k}\{R_{j,k}\} \quad \text{for } K > 1.$$

In this application, a single parameter is used to describe the objects with K=2, such that the summed term can be simplified to $$R_{j,k} = \frac{(n_j - 1)\sigma_j - (n_k - 1)\sigma_k}{(\mu_j - \mu_k)^2}$$

where $n_j$, $\mu_j$ and $\sigma_j$ are the number of objects, the mean and the standard deviation of cluster j. The splitting index k is chosen to maximize DB(K).

The nested structure of the clustering is captured by storing the indexes k in a tree at each step. DB(K) can also be used to choose overall partitioning of the tree, because for strongly clustered data it will be minimized at the "correct" number of clusters.

A desirable feature of this algorithm, not easily supported by other clustering methods, is that new objects (e.g., new EEG epochs as they are acquired) can be added to the end of the list without having to start over. Komzak (Komzak, Jiri, *Hierarchical clustering speed up using position lists and data position hierarchy*, www.kmi.open.ac.uk/papers/ kmi-tr-115.pdf, 2001) has developed a more general, but slower, O(N*N), method for speeding up clustering by using sorted objects.

Klatchko et al. (Klatchko, A., Raviv, G., Webber, W. R., and Lesser, R. P., *Enhancing the detection of seizures with a clustering algorithm*, Electroencephalogr. Clin. Neurophysiol 106: 52–63, 1998) apply clustering (via directed graph) to seizure detection to enhance an existing detector. Candidate seizure epochs are grouped together if they independently have a probability that exceeds a cutoff value, are in the same or neighboring channels, and occur simultaneously or sequentially. This method does not work when there are gaps, i.e., non-seizure epochs, in the sequence of candidate epochs. Because the grouping condition only considers proximal pairs of epochs, the same result can be achieved without clustering.

Figure 4:
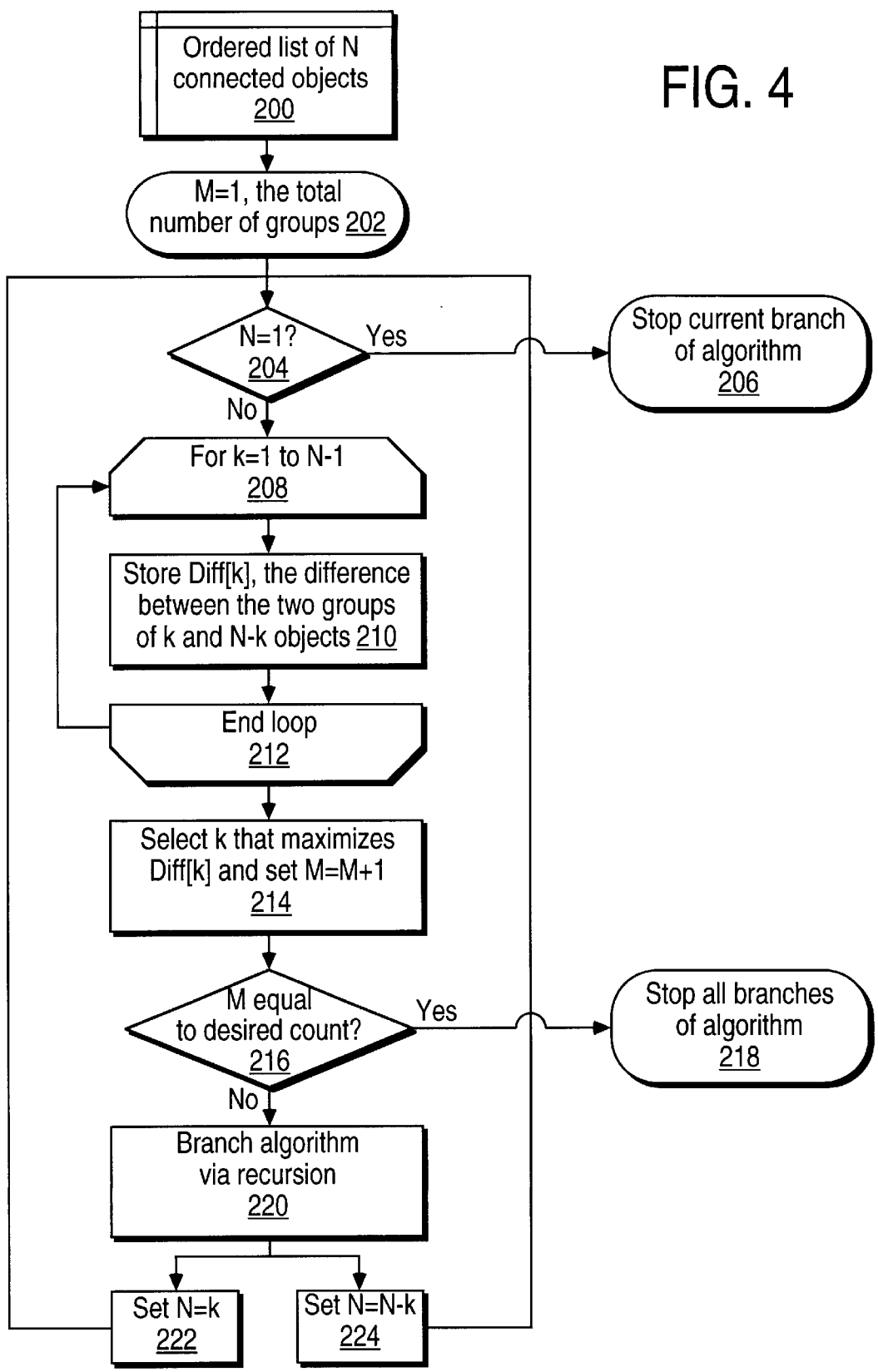
FIG. 4 is a flow chart illustrating an embodiment of connected-object clustering for establishing a seizure point according to the present invention.

FIG. 4 is a flow chart illustrating an example of a connected-object clustering algorithm with two branches in an embodiment according to the present invention. Initially, an ordered list of N connected objects is supplied to the algorithm as indicated by block 200. M, which is the total number of groups in the nested structure, is initially set to one, as indicated by block 202. The algorithm then determines whether N=1 as indicated by block 204, and the current branch of the algorithm is stopped if N=1, as indicated by block 206. If N is greater than 1, the algorithm enters an iterative loop as indicated by blocks 208, 210, and 212 in FIG. 4. Within this loop for k=1 to N−1, the difference between two groups of k and N−k objects is stored in the computer memory as Diff[k] until the end of the loop.

Subsequently, k is selected such that the difference Diff[k] between the two groups of k and N−k objects is maximized, and M is incremented by 1, as indicated by block 214 in FIG. 4. The connected-object clustering algorithm determines whether M is equal to a desired count as indicated by block 216, and stops all branches of the algorithm as indicated by block 218 if M is equal to the desired count. If M is not equal to the desired count, the algorithm is branched via recursion as indicated by block 220. One branch of the algorithm sets N=k as indicated by block 222 while another branch sets N=N−k as indicated by block 224. These two branches of the algorithm are then looped back to block 204 as illustrated in FIG. 4.

Referring back to FIG. 3, after the connected-object clustering algorithm is applied to the epochs in the sixty-second sliding window as indicated by block 114, a seizure point (SzPt) is established from the clustering result and described with neural network rules, as indicated by block 116. A determination is then made as to whether the seizure point is valid and better than a pre-existing seizure point, if any, as indicated by block 118. If the seizure point derived from the current waveform is better than a pre-existing seizure point established from a previous waveform, the current seizure point is then regarded as the "best" seizure point, as indicated by block 120. Otherwise, the pre-existing seizure point remains as the "best" seizure point. Subsequently, the matching pursuit, neural network rules and connected-object clustering algorithms as indicated by blocks 110, 112, and 114 are applied to other digitized waveforms in the montage of the EEG recording until all of the waveforms within the sixty-second sliding window for all channels of the montage are processed.

After all of the waveforms in the sixty-second sliding window of the montage are processed, one or more seizure events (SzEvts) are established by analyzing a plurality of proximal seizure points from the waveforms of the montage, as indicated by block 122 in FIG. 3. After a seizure event is established with the seizure points that are temporally close to each other from the waveforms of the montage, the algorithm determines whether such a seizure event (SzEvt) is valid, as indicated by block 124 in FIG. 3.

If the seizure event is valid, the computer notifies the user that a seizure has been identified, as indicated by block 126 in FIG. 3. The time of onset of the seizure and a description of the seizure based upon the EEG data, including, for example, the duration, type, and severity of the seizure, may be saved in the computer in an embodiment as indicated by block 128 in FIG. 3.

After all waveforms of the montage within a given sixty-second sliding window is processed, the sliding window is shifted by a small increment of time, for example, one second, until the whole EEG recording is processed, as indicated by blocks 130 and 132. If the EEG recording has been completely processed, the program ends as indicated by block 134. If the processing of the EEG recording has not been completed, one second is added to the time T and the sliding window is shifted by one second as indicated by block 132. The program then loops back to block 104 to process new EEG data within the newly shifted sixty-second window.

Figure 5:
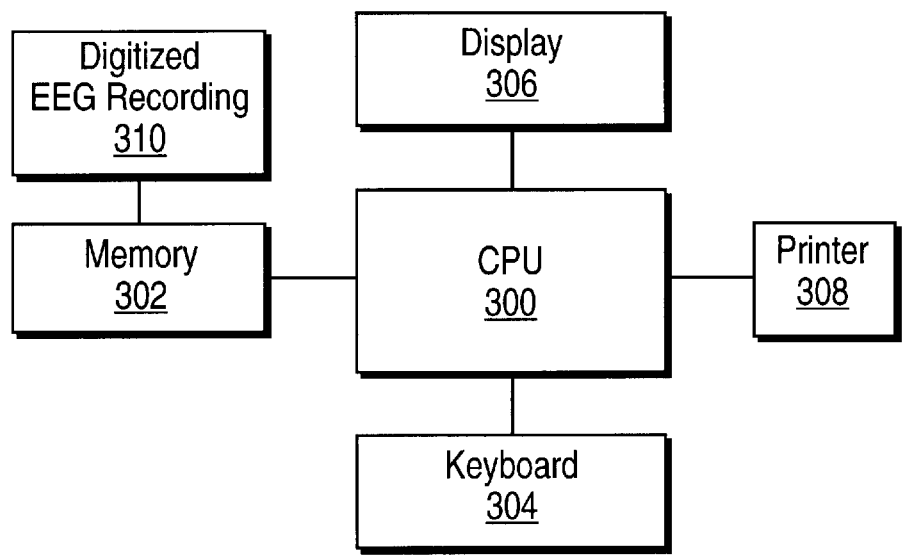
FIG. 5 is a block diagram illustrating a computer system for processing EEG recordings to identify seizure events in an embodiment according to the present invention.

FIG. 5 is a simplified block diagram illustrating a computer system or an article of manufacture for processing EEG data according to embodiments of the present invention. As illustrated in FIG. 5, the computer system includes a central processing unit (CPU) 300, a computer readable medium such as a memory 302, an input device such as a keyboard 304, and output devices such as a display monitor 306 and a printer 308. The digitized EEG recording 310 is read into the memory 302 for processing by the CPU 300, which is capable of running a computer program code comprising instructions for performing process steps that include matching pursuit, neural network rules, and connected-object clustering algorithms according to embodiments of the present invention.

From the above description of embodiments of the invention, it is manifest that various equivalents can be used to implement the concepts of the present invention without departing from its scope. Moreover, while the invention has been described with specific reference to certain embodiments, a person of ordinary skill in the art would recognize that changes can be made in form and detail without departing from the spirit and the scope of the invention. The described embodiments are to be considered in all respects as illustrative and not restrictive. It should also be understood that the invention is not limited to the particular embodiments described herein, but is capable of many equivalents, rearrangements, modifications, and substitutions without departing from the scope of the invention as set forth in the claims.

What is claimed is:

1. A method of detecting a seizure, comprising the steps of:
    a) dividing a digitized waveform of an electroencephalogram (EEG) recording into a plurality of epochs each having a first predetermined duration;
    b) computing matching pursuit for a given one of the epochs to obtain a plurality of seizure atoms;
    c) describing the seizure atoms and the given epoch with at least one neural network (NN) rule;
    d) applying connected-object clustering to the epochs in a sliding window of a second predetermined duration to obtain a clustering result; and
    e) establishing a seizure point from the clustering result.

2. The method of claim 1, further comprising the step of determining whether the seizure point is valid.

3. The method of claim 1, further comprising the steps of repeating steps (b)–(e) and determining whether a succeeding seizure point is better than a preceding seizure point.

4. The method of claim 1, wherein the first predetermined duration is less than the second predetermined duration.

5. The method of claim 4, wherein the first predetermined duration is about 2 seconds.

6. The method of claim 4, wherein the second predetermined duration is about 60 seconds.

7. The method of claim 1, further comprising the step of setting an initial time T=0 prior to the step of computing matching pursuit for the given epoch.

8. The method of claim 7, further comprising the steps of determining whether unprocessed EEG data is available at the time T, and causing a time delay of a third predetermined duration if unprocessed EEG data is unavailable at the time T.

9. The method of claim 8, wherein the digital waveform is one of a plurality of waveforms forming a montage of the EEG recording, the method further comprising the steps of obtaining a subsequent waveform of the EEG recording and repeating steps (b)–(e) if unprocessed EEG data is available at the time T.

10. The method of claim 9, further comprising the step of establishing a seizure event with a plurality of proximal seizure points from the waveforms of the montage.

11. The method of claim 10, further comprising the step of determining whether the seizure event is valid.

12. The method of claim 11, further comprising the step of notifying a user that a seizure is identified if the seizure event is valid.

13. The method of claim 12, further comprising the step of saving the time T and a description of the seizure.

14. The method of claim 11, further comprising the steps of adding a time of the third predetermined duration to the time T and shifting the sliding window by the time of the third predetermined duration until the EEG recording is finished.

15. The method of claim 14, wherein the third predetermined duration is about 1 second.

16. A computer readable medium comprising a plurality of instructions, which when executed by a computer, cause the computer to perform the steps of:
(a) dividing a digitized waveform of an electroencephalogram (EEG) recording into a plurality of epochs each having a first predetermined duration;
(b) computing matching pursuit for a given one of the epochs to obtain a plurality of seizure atoms;
(c) describing the seizure atoms and the given epoch with at least one neural network (NN) rule;
(d) applying connected-object clustering to the epochs in a sliding window of a second predetermined duration to obtain a clustering result; and
(e) establishing a seizure point from the clustering result.

17. The computer readable medium as set forth in claim 16, further comprising instructions which cause the computer to perform the step of determining whether the seizure point is valid.

18. The computer readable medium as set forth in claim 16, further comprising instructions which cause the computer to perform the steps of:
repeating steps (b)–(e); and
determining whether a succeeding seizure point is better than a preceding seizure point.

19. The computer readable medium as set forth in claim 16, wherein the first predetermined duration is less than the second predetermined duration.

20. The computer readable medium as set forth in claim 19, wherein the first predetermined duration is about 2 seconds.

21. The computer readable medium as set forth in claim 19, wherein the second predetermined duration is about 60 seconds.

22. The computer readable medium as set forth in claim 16, further comprising instructions which cause the computer to perform the step of setting an initial time T=0 prior to the step of computing matching pursuit for the given epoch.

23. The computer readable medium as set forth in claim 22, further comprising instructions which cause the computer to perform the steps of:
determining whether unprocessed EEG data is available at the time T; and
causing a time delay of a third predetermined duration if unprocessed EEG data is unavailable at the time T.

24. The computer readable medium as set forth in claim 23, wherein the digitized waveform is one of a plurality of waveforms of the EEG recording which includes a montage of multiple channels of simultaneous waveforms, the computer readable medium further comprising instructions which cause the computer to perform the steps of:
obtaining a subsequent waveform of the EEG recording; and
repeating steps (b)–(e) if unprocessed EEG data is available at the time T.

25. The computer readable medium as set forth in claim 24, further comprising instructions which cause the computer to perform the step of establishing a seizure event with a plurality of proximal seizure points from the waveforms of the montage.

26. The computer readable medium as set forth in claim 25, further comprising instructions which cause the computer to perform the step of determining whether the seizure event is valid.

27. The computer readable medium as set forth in claim 26, further comprising instructions which cause the computer to perform the step of notifying a user that a seizure is identified if the seizure event is valid.

28. The computer readable medium as set forth in claim 27, further comprising instructions which cause the computer to perform the step of saving the time T and a description of the seizure.

29. The computer readable medium as set forth in claim 26, further comprising instructions which cause the computer to perform the steps of:
adding a time of the third predetermined duration to the time T; and
shifting the sliding window by the time of the third predetermined duration until the EEG recording is finished.

30. The computer readable medium as set forth in claim 29, wherein the third predetermined duration is about 1 second.

31. An article of manufacture, including a computer readable medium having computer readable program code means embodied therein for detecting a seizure, the computer readable program code means in the article of manufacture comprising:
(a) computer readable program code means for dividing a digitized waveform of an electroencephalogram (EEG)

recording into a plurality of epochs each having a first predetermined duration;

(b) computer readable program code means for computing matching pursuit for a given one of the epochs to obtain a plurality of seizure atoms;

(c) computer readable program code means for describing the seizure atoms and the given epoch with at least one neural network (NN) rule;

(d) computer readable program code means for applying connected-object clustering to the epochs in a sliding window of a second predetermined duration to obtain a clustering result; and (e) computer readable program code means for establishing a seizure point from the clustering result.

32. The article of manufacture as set forth in claim 31, wherein the computer readable program code means further comprises computer readable program code means for determining whether the seizure point is valid.

33. The article of manufacture as set forth in claim 31, wherein the computer readable program code means further comprises:

computer readable program code means for repeating steps performed by computer readable program code means (b)–(e); and computer readable program code means for determining whether a succeeding seizure point is better than a preceding seizure point.

34. The article of manufacture as set forth in claim 31, wherein the first predetermined duration is less than the second predetermined duration.

35. The article of manufacture as set forth in claim 34, wherein the first predetermined duration is about 2 seconds.

36. The article of manufacture as set forth in claim 34, wherein the second predetermined duration is about 60 seconds.

37. The article of manufacture as set forth in claim 31, wherein the computer readable program code means further comprises computer readable program code means for setting an initial time T=0 prior to computing matching pursuit for the given epoch.

38. The article of manufacture as set forth in claim 37, wherein the computer readable program code means further comprises:

computer readable program code means for determining whether unprocessed EEG data is available at the time T; and computer readable program code means for causing a time delay of a third predetermined duration if unprocessed EEG data is unavailable at the time T.

39. The article of manufacture as set forth in claim 38, wherein the digitized waveform is one of a plurality of waveforms of the EEG recording which includes a montage of multiple channels of simultaneous waveforms, and wherein the computer readable program code means further comprises:

computer readable program code means for obtaining a subsequent waveform of the EEG recording; and computer readable program code means for repeating steps performed by computer readable program code means (b)–(e) if unprocessed EEG data is available at the time T.

40. The article of manufacture as set forth in claim 39, wherein the computer readable program code means further comprises computer readable program code means for establishing a seizure event with a plurality of proximal seizure points from the waveforms of the montage.

41. The article of manufacture as set forth in claim 40, wherein the computer readable program code means further comprises computer readable program code means for determining whether the seizure event is valid.

42. The article of manufacture as set forth in claim 41, wherein the computer readable program code means further comprises computer readable program code means for notifying a user that a seizure is identified if the seizure event is valid.

43. The article of manufacture as set forth in claim 42, wherein the computer readable program code means further comprises computer readable program code means for saving the time T and a description of the seizure.

44. The article of manufacture as set forth in claim 41, wherein the computer readable program code means further comprises:

computer readable program code means for adding the time of the third predetermined duration to the time T; and computer readable program code means for shifting the sliding window by the time of the third predetermined duration until the EEG recording is finished.

45. The article of manufacture as set forth in claim 44, wherein the third predetermined duration is about 1 second.

* * * * *